(12) United States Patent
LeHuec et al.

(10) Patent No.: US 7,828,807 B2
(45) Date of Patent: Nov. 9, 2010

(54) IMPLANTATION OF A DEFORMABLE PROSTHESIC DEVICE

(75) Inventors: Jean-Charles LeHuec, Pessac (FR); Mingyan Liu, Bourg la Reine (FR); Loic Josse, Denens (CH)

(73) Assignee: Warsaw Orthopedic, Inc., Warsaw, IN (US)

( * ) Notice: Subject to any disclaimer, the term of this patent is extended or adjusted under 35 U.S.C. 154(b) by 992 days.

(21) Appl. No.: 11/343,230

(22) Filed: Jan. 30, 2006

(65) Prior Publication Data

US 2007/0005088 A1 Jan. 4, 2007

Related U.S. Application Data

(63) Continuation of application No. 11/143,404, filed on Jun. 2, 2005, now abandoned.

(30) Foreign Application Priority Data

Apr. 29, 2005 (FR) ................... 05 04428

(51) Int. Cl.
*A61B 17/58* (2006.01)
(52) U.S. Cl. .............. 606/99; 606/93; 606/86 R; 414/218; 406/53; 137/246.15
(58) Field of Classification Search ............. 606/86 A, 606/99, 93; 414/218; 406/53; 137/246.15
See application file for complete search history.

(56) References Cited

U.S. PATENT DOCUMENTS

| 1,077,810 | A | * | 11/1913 | Craggs | .................. 222/413 |
| RE24,079 | E | * | 10/1955 | Mateer | ...................... 222/378 |
| 3,081,644 | A | * | 3/1963 | Hudgens et al. | ............ 74/89.42 |
| 3,743,140 | A | * | 7/1973 | Sauerbrey | .................... 222/63 |
| 4,582,097 | A | * | 4/1986 | Izzi et al. | ....................... 141/1 |
| 4,636,217 | A | | 1/1987 | Ogilvie et al. | |
| 4,648,285 | A | * | 3/1987 | Carson | .................... 74/424.92 |
| 4,811,618 | A | * | 3/1989 | Takayama | .................. 74/89.44 |
| 4,881,862 | A | * | 11/1989 | Dick | ......................... 414/218 |
| 4,964,314 | A | * | 10/1990 | Wilkes | ..................... 74/424.92 |
| 4,973,334 | A | | 11/1990 | Ziemann | |
| 5,071,040 | A | * | 12/1991 | Laptewicz, Jr. | ............. 222/235 |
| 5,171,280 | A | | 12/1992 | Baumgartner | |
| 5,263,927 | A | * | 11/1993 | Shlain | ......................... 604/13 |
| 5,577,850 | A | * | 11/1996 | Mishima | ...................... 401/83 |
| 5,645,597 | A | | 7/1997 | Krapiva | |
| 5,716,416 | A | | 2/1998 | Lin | |
| 5,919,235 | A | | 7/1999 | Husson et al. | |
| 6,019,765 | A | | 2/2000 | Thornhill et al. | |
| 6,062,438 | A | * | 5/2000 | Ellis et al. | ................... 222/349 |
| 6,090,063 | A | * | 7/2000 | Makower et al. | .............. 604/13 |
| 6,165,218 | A | | 12/2000 | Husson et al. | |

(Continued)

*Primary Examiner*—Thomas C Barrett
*Assistant Examiner*—David W Bates

(57) ABSTRACT

One embodiment is directed to instrumentation for performance of a spinal implantation procedure. In one form, this instrumentation includes: a tube device with an inner surface defining a passage from a proximal end portion to a distal end portion, a conveyor including a threaded conveying rod to be received in the passage of the tube device that can be rotated in the tube or moved in translation along the passage, and a deformable prosthesis structured to move through the passage of the tube by rotating the threaded conveying rod while at least a portion of the deformable prosthesis is positioned between the inner surface and the rod. Optionally, a tool to maintain position of the tube device can be included that has a jaw mechanism, among other things.

10 Claims, 3 Drawing Sheets

U.S. PATENT DOCUMENTS

| | | |
|---|---|---|
| 6,245,107 B1 | 6/2001 | Ferree |
| 6,264,659 B1 | 7/2001 | Ross et al. |
| 6,267,763 B1 | 7/2001 | Castro |
| 6,280,475 B1 | 8/2001 | Bao et al. |
| 6,547,465 B1 * | 4/2003 | Rago et al. .................... 401/17 |
| 6,579,291 B1 | 6/2003 | Keith et al. |
| 6,610,094 B2 | 8/2003 | Husson |
| 6,620,196 B1 | 9/2003 | Trieu |
| 6,660,006 B2 | 12/2003 | Markworth et al. |
| 6,660,037 B1 | 12/2003 | Husson et al. |
| 6,666,866 B2 | 12/2003 | Martz et al. |
| 6,689,125 B1 | 2/2004 | Keith et al. |
| 7,008,433 B2 * | 3/2006 | Voellmicke et al. ........... 606/93 |
| 7,014,640 B2 * | 3/2006 | Kemppainen et al. ..... 606/86 R |
| 2002/0082605 A1 | 6/2002 | Reiley et al. |
| 2002/0188295 A1 | 12/2002 | Martz et al. |
| 2003/0149438 A1 | 8/2003 | Nichols et al. |
| 2003/0216737 A1 | 11/2003 | Biscup |
| 2004/0024409 A1 | 2/2004 | Sand et al. |
| 2004/0024463 A1 | 2/2004 | Thomas, Jr. et al. |
| 2008/0051800 A1 * | 2/2008 | Diaz et al. .................... 606/92 |
| 2010/0044656 A1 * | 2/2010 | Imase ......................... 254/96 |

* cited by examiner

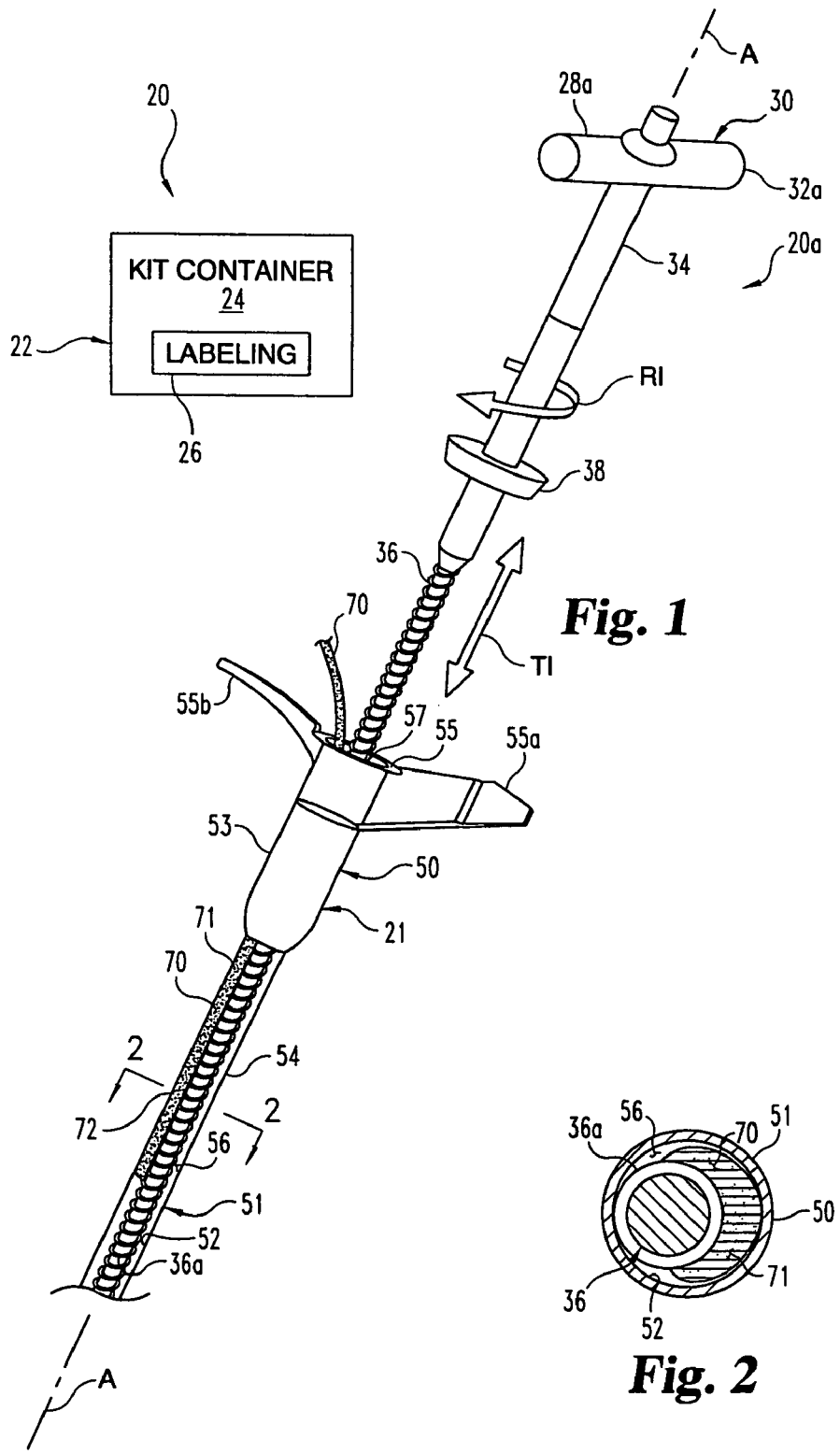

IMPLANTATION OF A DEFORMABLE PROSTHESIC DEVICE

CROSS-REFERENCE TO RELATED APPLICATIONS

This application is a continuation of U.S. patent application Ser. No. 11/143,404, filed Jun. 2, 2005 now abandoned, the contents of which are incorporated herein by reference in their entirety.

BACKGROUND

The present invention relates to prosthetic device implantation, and more particularly, but not exclusively, relates to techniques to insert a deformable spinal prosthesis and related instrumentation.

The use of prosthetic implants to address orthopedic injuries and ailments has become commonplace. Nonetheless, there is an ever-present challenge to enable less invasive surgical techniques, shorten the time required to surgically implant prosthetic devices, decrease surgery recovery time, and/or provide other improvements. Thus, there is a need for additional contributions in this area of technology.

SUMMARY

One embodiment of the present application is a unique technique to implant a deformable prosthetic device. Other embodiments include unique methods, systems, devices, kits, tools, instrumentation, and apparatus involving implantation of a deformable prosthetic device.

A further embodiment includes operating an instrument that percutaneously extends into a patient's body, the instrument including a tube, a threaded conveying rod extending inside the tube, a proximal end portion, and a distal end portion. The instrument is placed into position with the distal end portion in proximity to a spinal structure of the patient's body while the proximal end portion remains outside the patient's body. With a deformable prosthesis being positioned between the tube and the rod, it is moved through the tube by rotating the rod while in position. At least a portion of the prosthesis is deposited on the spinal structure with the instrument.

Various forms of this embodiment optionally include: reversing direction of rotation to change direction of deformable prosthesis movement through the tube, and/or turning a handle coupled to the rod to cause rod rotation. Alternatively or additionally this embodiment can optionally include: attaching a tool to the tube, maintaining location of the tube relative to the rod with the tool, and holding down the rod by engaging a travel stop fixed to the rod with a member connected to the tool.

Another embodiment is directed to a kit or system to perform a spinal implantation procedure. In one form, this kit includes: a tube device with an inner surface defining a passage from a proximal end portion to a distal end portion, a conveyor including a threaded conveying rod to be received in the passage of the tube device that can be rotated in the tube or moved in translation along the passage, and a deformable prosthesis structured to move through the passage of the tube by rotating the threaded conveying rod while at least a portion of the deformable prosthesis is positioned between the inner surface and the rod.

Still another embodiment includes instrumentation that comprises: a threaded conveying rod structured to rotate about an axis of rotation, a tube device including a tube extending along the axis of rotation and defining a passage therethrough to receive the rod, a handle coupled to a proximal end portion of the threaded conveying rod, and a travel stop structured to engage the tube device to limit at least one translational direction of travel of the rod along the axis. The rod is structured to rotate in response to rotation of the handle and to move in translation in response to movement of the handle along the axis of rotation and the tube is sized and shaped to have a distal end portion placed inside a body of a patient while a proximal end portion remains outside the body of the patient. The tube includes an accessway to the passage to receive a deformable prosthesis that can be inserted in the patient's body with the instrumentation.

One object of the present application is to provide a unique implantation technique.

Alternatively or additionally, another object of the present application is to provide a unique method, system, device, kit, tool, instrument, and/or apparatus involving implantation of a deformable prosthetic device.

Further embodiments, forms, features, aspects, benefits, objects, and advantages of the present application shall become apparent from the detailed description and figures provided herewith.

BRIEF DESCRIPTION OF THE DRAWING

FIG. 1 is a partial perspective view of an instrument to implant a deformable prosthesis in the spine of a patient.

FIG. 2 is cross sectional view of the instrument corresponding to section line 2-2 shown in FIG. 1.

DETAILED DESCRIPTION OF SELECTED EMBODIMENTS

Figure 3:
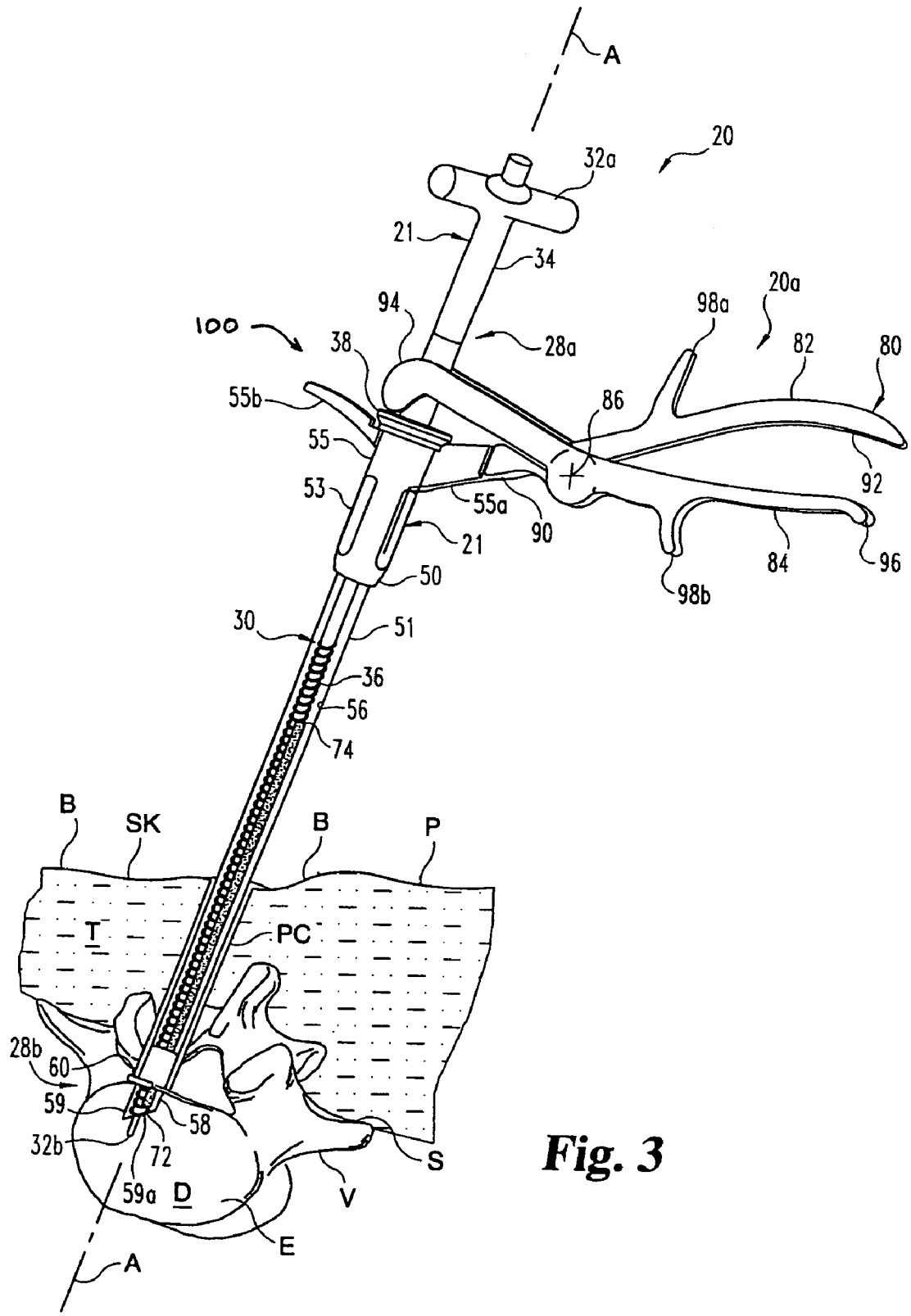
FIG. 3 is a perspective view of the instrument of FIG. 1 during insertion of a deformable prosthesis into the spine of a patient.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations or further modifications of the described embodiments, and any further applications of the principles of the invention as described herein are contemplated as would normally occur to one skilled in the art to which the invention relates.

FIG. 1 illustrates surgical implantation system 20, which includes instrumentation 20a. Instrumentation 20a includes implant insertion instrument 21 shown in a partial, perspective view. System 20 also schematically depicts kit 22 including packing or container 24 and labeling 26. Labeling 26 would typically provide instructions, warnings, and other information regarding the use of its contents. Instrument 21 can be provided in kit 22 along with other instrumentation and materials as will be further described hereinafter.

Figure 4:
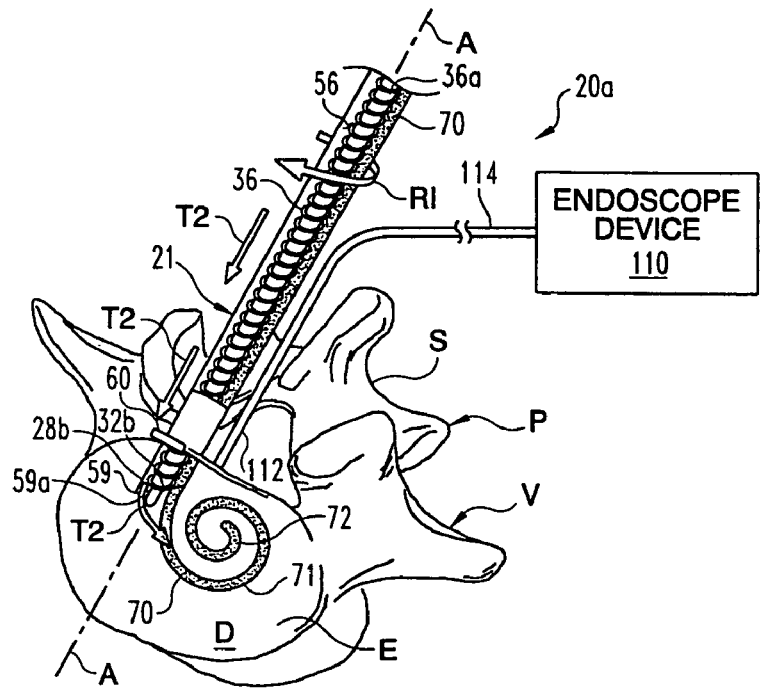
FIG. 4 is a partial, perspective view of the instrument of FIG. 1 with a greater portion of the prosthesis inserted into the spine as compared to FIG. 3.
Figure 5:
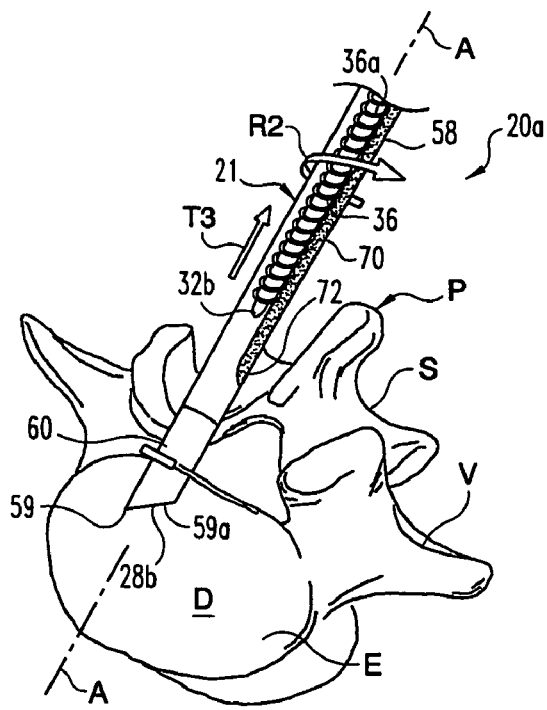
FIG. 5 is a partial, perspective view of the instrument of FIG. 1 illustrating retraction of the prosthesis.

Referring additionally to FIGS. 3-5, instrument 21 extends along longitudinal axis A and has proximal end portion 28a opposite distal end portion 28b. Distal end portion 28b is not designated in FIG. 1 because of the partial view of instrument 21 shown. Instrument 21 includes rotational conveyor 30 that has proximal end portion 32a opposite distal end portion 32b.

Along proximal end portion 32a, conveyor 30 includes T-shaped handle 34. Handle 34 is connected to threaded conveying rod 36. Rod 36 includes helical threading 36a that extends from proximal end portion 32a to distal end portion 32b. Travel stop 38 is fixed to conveyor 30 proximal to rod 36 and is in the shape of a circular portion of a cone.

Instrument 21 also includes tube device 50. Device 50 includes tube 51 having proximal end portion 53 opposite distal end portion 58 and inner surface 52 opposite outer surface 54. Inner surface 52 defines passage 56 through tube 51 that extends along axis A. At least a portion of tube 51 is transparent to visualize structure therein. Distal end portion 58 defines distal end 59 that is shaped to a point to assist with the passage of tube 51 through tissue. Distal end 59 defines distal opening 59a. Connected along distal end portion 58 is flange 60 that is provided to bear against hard tissue as shown in FIGS. 3-5. At proximal end portion 53, tube device includes head 55 that has protruding members 55a and 55b. Members 55a and 55b laterally extend away from axis A.

Referring specifically to FIGS. 1 and 3, conveyor 30 is arranged to rotate about axis A as designated by curved arrow R1 and can move in translation relative to axis A as designated by double-headed arrow T1. For the position of conveyor 30 relative to device 50 shown in FIG. 1, accessway 57 is provided in the form of an opening to passage 56 at the proximal end of head 55. In comparison, stop 38 engages head 55 in FIG. 3 because conveyor 30 has been repositioned relative to device 50 by translational movement along axis A. As a result, accessway 57 is closed in the view of FIG. 3. Correspondingly, further translational motion of conveyor 30 into tube 51 is limited by stop 38 when it engages head 55.

System 20 further includes deformable prosthesis 70 in the form of an elongated implant material 71. Prosthesis 70 can also be included in kit 22. Prosthesis 70 is loaded into passage 56 of instrument 21 through accessway 57 as illustrated in FIG. 1. Prosthesis 70 includes distal end portion 72 opposite proximal end portion 74 (see FIG. 3.). As prosthesis 70 is loaded, it is positioned between rod 36 and inner surface 52 of tube 51. Threading 36a contacts at least a portion of prosthesis 70, gaining purchase therewith. At the same time, at least a portion of prosthesis 70 that is in contact with threading 36a also contacts tube 51. Typically, as material 71 is positioned in this manner, it deforms and at least partly conforms to the surfaces it contacts. Referring also to FIG. 2, a cross-sectional view of this spatial relationship between rod 36, tube 51, and material 71 is shown that corresponds to section line 2-2 of FIG. 1, and for which like reference numerals refer to like features.

With prosthesis 70 disposed between rod 36 and tube 51 in this manner, rotation of rod 36 about axis A tends to move prosthesis 70 along axis A, operating as a screw or worm gear conveyance device. For rotation of rod 36 in the direction indicated by arrow R1, prosthesis 70 advances into tube 51 towards distal opening 59a. After prosthesis 70 is loaded into tube 51 and/or if there is a continuously open accessway for prosthesis (not shown), stop 38 can be distally advanced to engage head 55. For such placement, the distal end of rod 36 just passes through opening 59a of tube 51 and has its distal travel through tube 51 limited by this engagement between stop 38 and head 55. For this configuration, rotation of rod 36 about axis A can continue, providing further distal advancement of prosthesis 70 through tube 51 and out opening 59a. In some applications, it is desirable to maintain device 50 in a desired position as rod 36 rotates and/or to hold stop 38 in a rotational bearing relationship with head 55.

As shown in FIG. 3, scissor tool 80 of system 20 and instrumentation 20a provides such features. Tool 80 detachably engages member 55a of head 55 in a fixed relationship and stop 38 in an adjustable bearing relationship. Tool 80 can also be included in kit 22. Tool 80 includes member 82 and member 84 that are pivotally coupled together by coupling 86; where the cross hairs designate a corresponding pivot point. Member 82 includes distal connection 90 that attaches member 55a to member 82 in a fixed spatial relationship and is subject to selective detachment by the user. Opposite distal connection 90, member 82 includes proximal handle 92 with ear 98a to facilitate proper gripping by hand. Member 84 includes distal hold down portion 94 that is shown bearing against stop 38 corresponding to the closure of accessway 57. Opposite distal hold down portion 94, member 84 includes proximal handle 96 with ear 98b to facilitate proper gripping of tool 80 by hand.

After distal connection 90 of tool 80 is formed, handles 92 and 96 are brought together or squeezed by hand to engage a proximal bearing surface of stop 38 with distal hold down portion 94, which pivots about the indicated pivot point of coupling 86. Correspondingly, tool 80 provides adjustable jaw mechanism 100. The resulting downward pressure or force provided by mechanism 100 can be modulated to permit rotation of conveyor 30 about axis A as further described hereinafter. Tool 80 can be detached and/or portion 94 can pivot away to disengage stop 38 so that rod 36 can be pulled out of tube 51. With the separation of stop 38 and head 55, accessway 57 is opened.

FIG. 4 further depicts distal end portion 28a of instrument 21. In FIG. 4, material 71 is deposited on a spinal structure S of patient P through opening 59a of tube 51 by rotation of conveyor 30 in the direction indicated by arrow R1. Spinal structure S can include, but is not limited to, vertebra V with endplate region E, and intervertebral disk space D, just to set forth some representative examples. Instrumentation 20a of system 20 further includes endoscope device 110. Device 110 is of a standard variety that includes steerable view port 112 at a distal end of optic cable 114. The application of device 110 is further described in connection with the operation of system 20 as follows.

Referring generally to FIGS. 1-5, one mode of operating system 20 is next described. In this application, system 20 is utilized to perform a minimally invasive spinal implantation procedure on patient P. This procedure includes forming a percutaneous passage PC through body B of patient P that extends through skin SK and subcutaneous soft tissue T as illustrated in FIG. 3. For this example, at least a portion of a spinal disk in space D is removed so that it can be replaced by a prosthetic device at least partially comprised of prosthesis 70. Such removal can occur through passage PC and/or one or more other passages in body B of patient P. Endoscope device 110 can be used to visualize tissue dissection/removal via passage PC or otherwise. Tube device 50 of instrument 21 can be used to maintain and/or define passage PC between intervertebral disk space D and the patient's skin SK, and/or a different arrangement can be utilized.

With tube device 50 positioned through passage PC, instrument 21 is assembled after discal tissue removal is completed by inserting conveyor 30 into tube 51 with distal end portion 32b proceeding first. Before stop 38 engages head 55, advancement of conveyor 30 is halted to leave accessway 57 open and to load prosthesis 70 as previously described. Stop 38 is then moved to engage head 55 in a rotational bearing relationship. Tool 80 is connected to member 55a of head 55 before, during, or after loading of material 71 of prosthesis 70. After head 55 is engaged by stop 38, hold down portion 94 of tool 80 is used to maintain such engagement. Tool 80 otherwise can be used to maintain position of device 50 as conveyor 30 is rotated therein with handle 34 to advance prosthesis 70 towards distal opening 59a of tube 51.

With specific reference to FIG. 4, device 110 can be used to visualize the deposition of material 71 of prosthesis 70 on spinal structure S with view port 112 extending through passage PC or through another percutaneous route. Advancement of material 71 is represented by arrows T2 as rod 36 is rotated about axis A in the direction indicated by arrow R1.

During the procedure, the need to remove or retract some or all of material 71 can arise. By reversing rotational direction of conveyor to turn in the opposite rotational direction as represented by arrow R2 in FIG. 5, material 71 can be retracted from space D and back into tube 51 as represented by arrow T3. Once prosthesis 70 is fully retracted into tube 51, hold down portion 94 of tool 80 can be released and conveyor 30 can be proximally withdrawn from device 50 to correspondingly withdraw prosthesis 70. Adjustments can be performed to continue the procedure as needed. Once prosthesis 70 is in position relative to the spine of patient P, suturing of it can take place or it is otherwise secured as needed using standard techniques.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. A method, comprising:
    operating an instrument that percutaneously extends into a patient's body, the instrument including a tube, a threaded conveying rod extending inside the tube, a proximal end portion and a distal end portion;
    placing the instrument into a position with the distal end portion in proximity to a spinal structure of the patient's body while the proximal end portion remains outside the patient's body;
    with a deformable prosthesis including an elongate implant material extending along a longitudinal axis between a distal end and an opposite proximal end, the elongate implant material being positioned between an inner surface of the tube and threading on the rod in purchase with the elongate implant material of the prosthesis so that the longitudinal axis of the implant material is offset from a longitudinal axis of the rod, moving the deformable prosthesis through the tube by rotating the rod while in the position; and
    depositing at least a portion of the elongate implant material of the prosthesis on the spinal structure with the instrument.

2. The method of claim 1, which includes reversing direction of said rotating to change direction of the moving of the deformable prosthesis through the tube so that the elongate implant material retracts from the spinal structure.

3. The method of claim 1, which includes turning a handle coupled to the rod to perform said rotating.

4. The method of claim 1, which includes:
    attaching a tool to the tube;
    maintaining location of the tube relative to rod during said rotating; and
    holding down the rod by engaging a travel stop fixed to the rod in rotating bearing relationship with a member connected to the tool.

5. The method of claim 1, which includes:
    forming a percutaneous passageway through the patient's body;
    inserting the instrument through the passageway; and
    visualizing said operating of the instrument with an endoscope device.

6. The method of claim 1, which includes passing the deformable prosthesis through an accessway to the passage in the tube.

7. The method of claim 6, which includes:
    closing the accessway by moving the rod in translation along an axis in a first direction; and
    opening the accessway by moving the rod in translation along the axis in a second direction opposite the first direction.

8. The method of claim 1, wherein the rod and elongate implant material are positioned eccentrically in the tube.

9. The method of claim 1, wherein the elongate implant material is continuous between its proximal and distal ends.

10. The method of claim 1, wherein moving the deformable prosthesis through the tube by rotating the rod while in the position includes advancing the distal end of the elongate material through the tube while advancing the proximal end of the elongate material from a location outside the tube into the tube by rotating the rod.

* * * * *